(12) United States Patent
Ikura et al.

(10) Patent No.: US 7,169,273 B2
(45) Date of Patent: Jan. 30, 2007

(54) ENZYME ELECTRODE

(75) Inventors: Yoshiaki Ikura, Fuji (JP); Masayuki Nomura, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 553 days.

(21) Appl. No.: 10/344,340

(22) PCT Filed: Sep. 25, 2001

(86) PCT No.: PCT/JP01/08311

§ 371 (c)(1),
(2), (4) Date: Feb. 11, 2003

(87) PCT Pub. No.: WO02/25262

PCT Pub. Date: Mar. 28, 2002

(65) Prior Publication Data

US 2003/0178998 A1    Sep. 25, 2003

(30) Foreign Application Priority Data

Sep. 25, 2000  (JP) ............................. 2000-291011

(51) Int. Cl.
*G01N 27/02*  (2006.01)
*C12Q 1/26*  (2006.01)
(52) U.S. Cl. ............... 204/403.14; 324/448; 205/777.5
(58) Field of Classification Search ............... None
See application file for complete search history.

(56) References Cited

U.S. PATENT DOCUMENTS 4,758,323 A * 7/1988 Davis et al. ........... 204/403.14

FOREIGN PATENT DOCUMENTS

| JP | 60-17347 A | 1/1985 |
|---|---|---|
| JP | 60-47698 A | 3/1985 |
| JP | 61-122560 A | 6/1986 |
| JP | 61-269058 A | 11/1986 |
| JP | 2-195241 A | 8/1990 |
| JP | 3-251195 A | 11/1991 |
| JP | 6-88805 A | 3/1994 |
| JP | 8-160049 A | 6/1996 |
| JP | 2517153 | 8/1996 |
| JP | 8-336397 A | 12/1996 |
| JP | 9-229895 A | 9/1997 |
| JP | 2000-189188 A | 7/2000 |
| JP | 2000-189197 A | 7/2000 |

OTHER PUBLICATIONS

C.K. Yu and L.S. Dietrich (1972) "Purification and properties of yeast nicotinamide adenine dinucleotide synthetase," Journal of Biological Chemistry vol. 247, pp. 4794-4802.*
"Glucose oxidase/hexokinase electrode for the determination of ATP[1]" by Dario Compagnone et al., *Analytica Chimica Acta*, 1997, vol. 340, pp. 109-113.
Fukyuban Sensa Gijyutu (Sensor Technology, Popularized version), published by Fuji Technosystem Co. Ltd., Japan (1976), p. 332.
"Enzyme Electrodes for ADP/ATP with Enhanced Sensitivity due to Chemical Amplification and Intermediate Accumulation", *Electroanalysis*, 1991, vol. 3, pp. 569-663.

* cited by examiner

*Primary Examiner*—Cecilia J. Tsang
*Assistant Examiner*—Christina Bradley
(74) *Attorney, Agent, or Firm*—Birch, Stewart, Kolasch & Birch, LLP

(57) ABSTRACT

Disclosed is an enzyme electrode comprising an electrode system comprising an insulating substrate having formed thereon a working electrode, a counter electrode and optionally a reference electrode, and a reaction layer formed on the electrode system, wherein the reaction layer comprises diaphorase (DI), 12α-hydroxysteroid dehydrogenase (12α-HSD) and nicotinamide adenine dinucleotide synthetase (NADS), at least a portion of the reaction layer being superposed on the working electrode, wherein the DI, 12α-HSD and NADS contained in the reaction layer are immobilized on the surface of the working electrode, so that a compound generated in the reaction layer can reach the surface of the working electrode. Also disclosed are a method for and a system for determining the concentration of adenosine triphosphate (ATP) in a sample by using the above-mentioned enzyme electrode.

7 Claims, 5 Drawing Sheets

ENZYME ELECTRODE

This application is the national phase under 35 U.S.C. § 371 of PCT International Application No. PCT/JP01/08311 which has an International filing date of Sep. 25, 2001, which designated the United States of America.

BACKGROUND OF THE INVENTION

1. Field of the Invention

The present invention relates to an enzyme electrode. More particularly, the present invention is concerned with an enzyme electrode comprising: (a) an electrode system comprising an insulating substrate having formed thereon a working electrode, a counter electrode and optionally a reference electrode; and (b) a reaction layer formed on the electrode system, wherein the reaction layer comprises diaphorase (DI), 12α-hydroxysteroid dehydrogenase (12α-HSD) and nicotinamide adenine dinucleotide synthetase (NADS), at least a portion of the reaction layer being superposed on the working electrode, wherein the DI, 12α-HSD and NADS contained in the above-mentioned portion of the reaction layer are immobilized on the surface of the working electrode, so that a compound generated in the reaction layer can reach the surface of the working electrode.

In addition, the present invention is concerned with a method for determining the concentration of adenosine triphosphate (ATP) by using the above-mentioned enzyme electrode, and also concerned with a system, which comprises the above-mentioned enzyme electrode, for determining the concentration of ATP.

The enzyme electrode of the present invention is advantageous for miniaturizing an apparatus for determining the concentration of ATP. Further, by the use of the enzyme electrode of the present invention, it has become possible to perform determination of the ATP concentration of a sample easily and rapidly, with high sensitivity, without the need of a cumbersome pretreatment.

2. Prior Art

Adenosine triphosphate (ATP) is a compound which is almost ubiquitously present in many living organisms.

Many chemical reactions occurring in a living body are performed utilizing the energy which is released during the generation of adenosine diphosphate (ADP) or adenosine monophosphate (AMP) by the hydrolysis of ATP. Further, in a living body, ATP is used as a precursor for a ribonucleic acid (RNA) and as a phosphate donor for phosphorylation in vivo.

Accordingly, ATP is a compound which plays a very important role in a living body and, thus, a quantitative analysis of ATP is important in various fields.

For example, in the field of food hygiene and sanitation, the ATP concentration is used as an index of the degree of contamination with microorganisms (such as bacteria) or with remnants of food which are likely to be causative of microbial contamination.

When microorganisms or food remnants are attached to foods or equipments, such as tablewares, kitchen utensils and food processing machines, the amount of ATP detected from the surface of the foods or equipments becomes increased by ATP derived from the microorganisms or food remnants. Therefore, samples obtained from the surface of the foods or equipments are subjected to a quantitative analysis of ATP to thereby determine the degree of contamination. It is considered that the higher the ATP concentration of a sample, the higher the degree of contamination with the microorganisms or with food remnants.

Since the amount of ATP in a sample is very small, a highly sensitive method for accurately determining the ATP concentration is necessary for determining the degree of contamination. As a method for determining the degree of contamination, there is known a method which uses the luciferin-luciferase reaction for determining the ATP concentration. This method involves the steps of reacting luciferin and luciferase with ATP extracted from a sample to thereby cause luminescence, and determining the degree of contamination of the sample from the intensity of luminescence.

In this method, the degree of contamination is determined using a calibration curve which shows the correlation between the intensity of luminescence and the degree of contamination, wherein the calibration curve is prepared by conducting the above-mentioned steps with respect to several standard samples having predetermined degrees of contamination.

The method based on the luciferin-luciferase reaction is performed using an expensive apparatus which is generally large and, hence, difficult to move. Accordingly, the above-mentioned method cannot be suitably used in the analyses in which the transfer of the apparatus is necessary. For example, the above-mentioned method is inapplicable to field analyses in which an analytical apparatus needs to be moved to the outdoors or the place to be protected from microbial contamination so that a desired analysis can be performed there.

Further, in this method, ATP is detected by using an optical technique and, consequently, there is a drawback in that an electric power consumption of the apparatus used for the analysis is large.

In addition, it is generally difficult to analyze a turbid sample by such an analytical method using an optical technique. Therefore, the above-mentioned method is inappropriate for analyzing a highly turbid sample, e.g. milk or blood, as such and, before the analysis of such a turbid sample, there is a need to dilute the sample or subject the sample to a pretreatment for removing or dissolving the insoluble microparticles which are causative of the turbidity. As a result, this method is accompanied by problems, such as cumbersomeness and low sensitivity.

In this situation, an enzyme electrode for quantitative analysis of ATP is receiving attention as an apparatus which not only can be easily moved, but also can be operated with a small electric power consumption and which is compact and is capable of directly analyzing highly turbid samples.

An enzyme electrode is a type of a so-called biosensor, and it is a device in which a change in the amount of a substance caused by an enzyme reaction is converted into electric signals by an electrochemical technique. Detection and measurement of a specific substance can be conducted using the electric signals.

Methods for determining the concentration of a specific substance in a sample by using an enzyme electrode are well known in the art. These methods are recently receiving attention due to their advantageous features, such as rapidness, easiness and economical advantages, and the use of enzyme electrodes in the field of clinical examination and the like are beginning to expand.

Unlike the analysis based on an optical technique, analysis using an enzyme electrode is advantageous in that even a turbid sample as such can be analyzed without the need of dilution thereof and the like and, hence, the analysis can be performed with very simple operations.

An example of an enzyme electrode well known in the art is an enzyme electrode for determining the glucose concentration of a blood sample (see Japanese patent No. 2517153). This enzyme electrode comprises: an electrode system comprising an insulating substrate having formed thereon a working electrode and a counter electrode, wherein the electrodes are prepared by screen printing and the like; an insulating layer formed on the electrode system (the insulating layer is used to maintain the surface areas of the exposed portions of the electrodes at a predetermined value); and an enzyme reaction layer comprising a hydrophilic polymer, an oxidoreductase and an electron carrier which is formed on the electrode system.

As an enzyme electrode for the quantitative analysis of ATP, an enzyme electrode employing glucose oxidase and hexokinase has been proposed (see Unexamined Japanese Patent Application Laid-Open Specification No. Sho 60-17347 (corresponding to U.S. Pat. Nos. 4,711,245 and 4,758,323) and Analytica Chimica Acta, 1997, vol. 340, pp. 109–113).

Glucose oxidase promotes the oxidation of glucose, and hexokinase employs ATP as a phosphate donor to promote the phosphorylation of glucose. Since both of the enzymes use glucose as their substrate, the above-mentioned two enzyme reactions (former and latter reactions) proceed simultaneously when the enzyme electrode is used for analyzing ATP in a sample, and the number of the latter reactions occurring in the enzyme electrode increases in accordance with the increase in the amount of ATP in the sample. For analyzing ATP, the above-mentioned enzyme electrode utilizes this phenomenon.

As another type of enzyme electrode for the quantitative analysis of ATP, there is known an enzyme electrode which uses adenosine triphoshatase (ATPase) and a hydrogen ion-sensitive field-effect transistor (pH-ISFET) (see Unexamined Japanese Patent Application Laid-Open Specification Nos. Sho 61-122560 and Sho 61-269058).

A pH-ISFET is a semiconductor element having a function to convert the change in the hydrogen ion concentration into electric signals.

Hydrogen ions are generated during the hydrolysis of ATP by ATPase, and this leads to an increase in the hydrogen ion concentration. The above-mentioned enzyme electrode is a device which converts such increase in the hydrogen ion concentration into electric signals by means of pH-ISFET, and the electric signals are used to determine the amount of ATP.

With respect to the enzyme electrodes mentioned above, the measuring sensitivity to ATP was only about $10^{-4}$ M to $10^{-5}$ M (see page 332 of "Fukyuban Sensa Gijyutu (Sensor Technology, Popularized version)" published by Fuji Technosystem Co. Ltd., Japan (1976)), and such enzyme electrodes were inappropriate for practical use.

As an example of enzyme electrodes which have sufficient sensitivity for use in the quantitative analysis of ATP, there can be mentioned an enzyme electrode which uses pyruvate kinase, hexokinase and glucose-6-phosphate dehydrogenase (Electroanalysis, 1991, vol. 3, pp. 659–663).

In this enzyme electrode, pyruvate kinase and hexokinase are used to conduct an enzymatic cycling of ATP/ADP system so as to enhance the sensitivity of the enzyme electrode. An enzymatic cycling is a method for enhancing the sensitivity of a measurement in which a change in the amount of a substance is amplified by using a combination of two or more enzymes.

In the above-mentioned enzyme electrode, glucose 6-phosphate and ADP are produced from glucose and ATP by hexokinase, and the change in the amount of glucose 6-phosphate by the production thereof is converted into electric signals.

On the other hand, pyruvate kinase catalyzes the reproduction of ATP from the produced ADP and, then, the reproduced ATP is subjected to the above-mentioned enzyme reaction by hexokinase.

The repetition of these two reactions leads to an increase in the amount of glucose 6-phosphate produced by the enzyme reaction, which increase is proportional to the amount of ATP in an analyzed sample. As a result, the sensitivity of the enzyme electrode is enhanced so as to enable a quantitative analysis of a small amount of ATP which has conventionally been undetectable. With respect to the determination of ATP by using this enzyme electrode, it has been reported that the measuring sensitivity to ATP is approximately $10^{-9}$ M.

However, this enzyme electrode has the following problems.

Hexokinase used in this enzyme electrode is an allosteric enzyme and the enzyme reaction rate of such an enzyme is difficult to control because the enzyme activity is easily influenced by substances other than its substrate. Therefore, a quantitative analysis of ATP has been difficult, especially when the ATP concentration of the sample is low.

Further, in this enzyme electrode, the enzymes are immobilized by an inclusion method which uses a gelatin membrane. When such an enzyme electrode is used for the analysis, in order to prepare a uniform sample solution and to facilitate the penetration of the sample solution into the gelatin membrane containing the enzymes, it is necessary to produce a flow of the sample solution by means of an agitator or stirrer. As a consequence, miniaturization of an apparatus employing the above-mentioned enzyme electrode has been difficult.

As mentioned above, an enzymatic cycling of ATP/ADP system is conducted in this enzyme electrode. Since both of ADP and ATP are involved in this enzymatic cycling, the analysis performed using this enzyme electrode is influenced by the concentration of ADP in the sample. Therefore, in order to selectively determine the ATP concentration of a sample containing both of ATP and ADP, it is necessary to conduct a cumbersome pretreatment for removing ADP from the sample.

As apparent from the above, there has been no conventional enzyme electrode which can be used for easily and rapidly performing a highly sensitive determination of the concentration of ATP in a sample.

SUMMARY OF THE INVENTION

In this situation, the present inventors have made extensive and intensive studies with a view toward developing an enzyme electrode which can be used for easily and rapidly conducting a determination of the ATP concentration of a sample, with high sensitivity, without the need of a cumbersome pretreatment. As a result, it has unexpectedly been found that, when an enzyme electrode comprises a reaction layer comprising diaphorase, 12α-hydroxysteroid dehydrogenase and nicotinamide adenine dinucleotide synthetase, such an enzyme electrode enables a highly sensitive and rapid determination of the concentration of ATP in a sample.

Further, the present inventors have found that, when the concentration of ATP in a sample is determined using the above-mentioned enzyme electrode, the enzyme electrode is free from the influence of ADP coexisting in the sample and, thus, a cumbersome pretreatment is unnecessary, and the determination of the ATP concentration can be performed with very simple operations.

The present invention has been completed, based on the above-mentioned novel findings.

Accordingly, it is an object of the present invention to provide an enzyme electrode which can be used for easily conducting a highly sensitive determination of the concentration of ATP in a sample.

It is another object of the present invention to provide a method for determining the concentration of ATP in a sample by using the above-mentioned enzyme electrode.

It is still another object of the present invention to provide a system, which comprises the above-mentioned enzyme electrode, for determining the concentration of ATP in a sample.

The foregoing and other objects, features and advantages of the present invention will be apparent to those skilled in the art from the following detailed description and the appended claims taken in connection with the accompanying drawings.

BRIEF DESCRIPTION OF THE DRAWINGS

In the drawings:

FIGS. 1(a) to 1(c) are schematic diagrams showing the steps involved in the production of the electrode system used in Examples 1 and 2 and Reference Examples 2 to 4, wherein:

FIG. 1(a) is a schematic diagram of an insulating substrate, wherein electric leads 2,2 are formed on the surface of insulating substrate 1, FIG. 1(b) is a schematic diagram of an electrode system precursor which is obtained by forming working electrode 3 and counter electrode 4, respectively, in association with electric leads 2 and 2 shown in FIG. 1(a), and FIG. 1(c) is a schematic diagram of an electrode system which is obtained by forming insulating layer 5 on the electrode system precursor shown in FIG. 1(b) at its surface portion except those surface portion which correspond to the terminal portions of electric leads 2 and 2, whole portion of working electrode 3 and whole portion of counter electrode 4;

DESCRIPTION OF REFERENCE NUMERALS

Figure 1A:
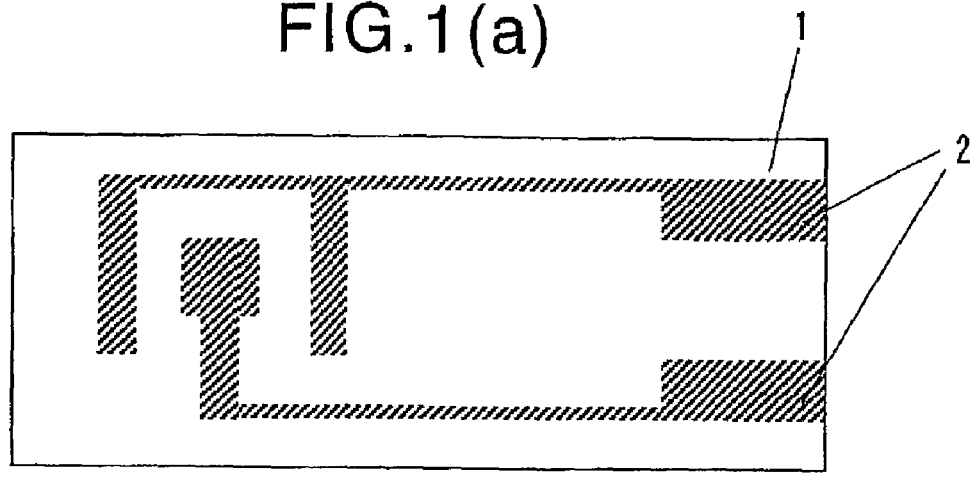
Figure 1B:
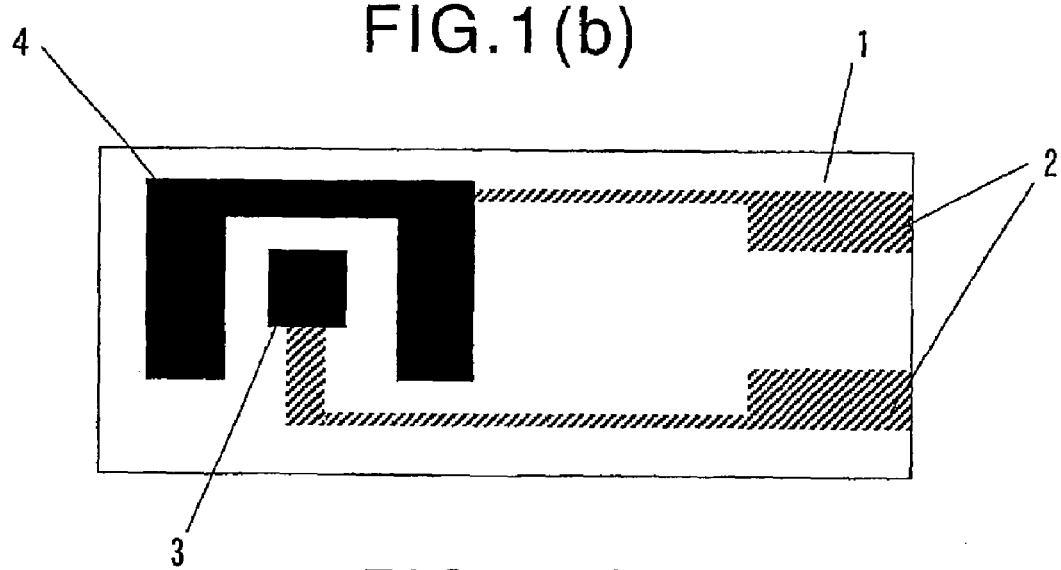

In FIGS. 1(a) to 1(c) and FIG. 2, the reference numerals are defined as follows.
1: Insulating substrate
2: Electric lead
3: Working electrode
4: Counter electrode
5: Insulating layer

DETAILED DESCRIPTION OF THE INVENTION

According to the present invention, there is provided an enzyme electrode comprising:
(a) an electrode system comprising an insulating substrate having formed thereon a working electrode, a counter electrode and optionally a reference electrode; and
(b) a reaction layer formed on the electrode system, wherein the reaction layer comprises diaphorase (DI), 12α-hydroxysteroid dehydrogenase (12α-HSD) and nicotinamide adenine dinucleotide synthetase (NADS),
at least a portion of the reaction layer being superposed on the working electrode, wherein the DI, 12α-HSD and NADS contained in the portion of the reaction layer are immobilized on the surface of the working electrode, so that a compound generated in the reaction layer can reach the surface of the working electrode.

For easy understanding of the present invention, the essential features and various embodiments of the present invention are enumerated below.
1. An enzyme electrode comprising:
(a) an electrode system comprising an insulating substrate having formed thereon a working electrode, a counter electrode and optionally a reference electrode; and
(b) a reaction layer formed on the electrode system, wherein the reaction layer comprises diaphorase (DI), 12α-hydroxysteroid dehydrogenase (12α-HSD) and nicotinamide adenine dinucleotide synthetase (NADS),
at least a portion of the reaction layer being superposed on the working electrode, wherein the DI, 12α-HSD and NADS contained in the portion of the reaction layer are immobilized on the surface of the working electrode, so that a compound generated in the reaction layer can reach the surface of the working electrode.
2. The enzyme electrode according to item 1 above, which further comprises a hydrophilic polymer layer, the hydrophilic polymer layer being interposed between the working electrode and the reaction layer and being in contact with both of the working electrode and the reaction layer.
3. The enzyme electrode according to item 1 or 2 above, wherein, with respect to the portion of the reaction layer which is superposed on the working electrode:
the total amount of proteins is 2.5 mg or less per $cm^2$ of the portion of the reaction layer;
the amount of DI in terms of the activity thereof is 0.25 U or more per $cm^2$ of the portion of the reaction layer;
the amount of 12α-HSD in terms of the activity thereof is 0.63 U or more per $cm^2$ of the portion of the reaction layer; and
the amount of NADS in terms of the activity thereof is 0.063 U or more per $cm^2$ of the portion of the reaction layer.
4. The enzyme electrode according to any one of items 1 to 3 above, wherein, with respect to the portion of the reaction layer which is superposed on the working electrode:
the total amount of proteins is 1.5 mg or less per $cm^2$ of the portion of the reaction layer;
the amount of DI in terms of the activity thereof is 1.0 U or more per $cm^2$ of the portion of the reaction layer;
the amount of 12α-HSD in terms of the activity thereof is 2.5 U or more per $cm^2$ of the portion of the reaction layer; and the amount of NADS in terms of the activity thereof is 0.25 U or more per cm² of the portion of the reaction layer.
5. The enzyme electrode according to any one of items 1 to 4 above, wherein, with respect to the portion of the reaction layer which is superposed on the working electrode:
the total amount of proteins is 1.1 mg or less per cm² of the portion of the reaction layer;
the amount of DI in terms of the activity thereof is 2.5 U or more per cm² of the portion of the reaction layer;
the amount of 12α-HSD in terms of the activity thereof is 6.25 U or more per cm² of the portion of the reaction layer; and
the amount of NADS in terms of the activity thereof is 0.625 U or more per cm² of the portion of the reaction layer.
6. A method for determining the concentration of adenosine triphosphate (ATP) in a sample, which comprises:
mixing a sample with an aqueous solution containing nicotinic acid adenine dinucleotide, a bile salt, an electron carrier and at least one member selected from the group consisting of ammonia and ammonium ion, to thereby obtain a sample solution;
contacting the sample solution with the working electrode, counter electrode and optionally reference electrode of the enzyme electrode of any one of items 1 to 5 above, to thereby form an electric circuit through the sample solution;
measuring the electric current at the working electrode while applying a voltage to the enzyme electrode between the working electrode thereof and the counter electrode thereof or between the working electrode thereof and the reference electrode thereof to thereby perform an oxidation reaction of the electron carrier on the surface of the working electrode, wherein when the enzyme electrode does not contain a reference electrode, the voltage is applied between the working electrode and the counter electrode and wherein when the enzyme electrode contains a reference electrode, the voltage is applied between the working electrode and the reference electrode; and
calculating the amount of ATP, based on the measured value of the electric current at the working electrode.
7. A system for determining the concentration of adenosine triphosphate (ATP) in a sample, wherein the concentration of ATP is determined using nicotinic acid adenine dinucleotide, a bile salt, an electron carrier and at least one member selected from the group consisting of ammonia and ammonium ion,
the system comprising:
the enzyme electrode of any one of items 1 to 5 above;
means for applying a voltage to the enzyme electrode between the working electrode thereof and the counter electrode thereof or between the working electrode thereof and the reference electrode thereof, the voltage being sufficient to perform an oxidation reaction of the electron carrier on the surface of the working electrode; and
means for measuring the electric current at the working electrode.
8. The system according to item 7 above, which further comprises means for calculating the amount of ATP, based on the measured value of the electric current at the working electrode.

Hereinbelow, the present invention will be described in detail.

The enzyme electrode of the present invention comprises:
(a) an electrode system comprising an insulating substrate having formed thereon a working electrode, a counter electrode and optionally a reference electrode; and
(b) a reaction layer formed on the electrode system, wherein the reaction layer comprises diaphorase (DI), 12α-hydroxysteroid dehydrogenase (12α-HSD) and nicotinamide adenine dinucleotide synthetase (NADS),
at least a portion of the reaction layer being superposed on the working electrode, wherein the DI, 12α-HSD and NADS contained in the portion of the reaction layer are immobilized on the surface of the working electrode, so that a compound generated in the reaction layer can reach the surface of the working electrode.

First, the electrode system (a) is explained in detail.

An insulating substrate of the electrode system (a) is obtained by molding an electric insulating material into a plate form. With respect to the shape of the insulating substrate, there is no particular limitation, and use can be made of any arbitrarily selected shapes.

It is preferred that the electric insulating material has excellent water resistance, heat resistance and chemical resistance. In addition, it is especially preferred that the electric insulating material exhibits excellent adhesive properties with conductive materials which are used as raw materials for electrodes and electric leads mentioned below.

Examples of electric insulating materials include insulating polymers, such as polyethylene terephthalate, polyethylene naphthalate, polyethylene sulfide, polycarbonate, polyallylate, polyether sulfide, polyimide and a urea resin; a glass, quartz, ceramics and a paper.

The above-mentioned electrode system (a) can be obtained by forming a working electrode, a counter electrode and optionally a reference electrode on the insulating substrate (hereinafter, the working, counter and reference electrodes are frequently referred to collectively as "electrodes").

In general, a reference electrode is not necessarily incorporated in the enzyme electrode of the present invention, and an electrode system containing only a working electrode and a counter electrode functions satisfactorily. However, when the enzyme electrode of the present invention comprises a reference electrode, it becomes possible to determine the ATP concentration with higher accuracy.

In the present invention, a thin membrane of a conductive material which is formed on the insulating substrate is generally used as an electrode.

Examples of conductive materials include carbon, gold, platinum, silver, silver chloride, iron, zinc, nickel and palladium. These materials can be used individually or in combination.

For forming the electrodes, there can be used a spattering method, an ion plating method, photolithography, a vacuum deposition method, a chemical vacuum deposition (CVD) method and an electrolytic method.

Further, the electrodes can be formed by applying to the surface of the insulating substrate a paste containing a conductive material in a microparticulate form. A method in which a paste ink (for example, a carbon paste ink or a silver paste ink) containing a conductive material in a microparticulate form is used to print the electrodes on the insulating substrate by screen printing and the like is especially preferred because, by this method, the electrode system can be produced rapidly and at low cost. Further, when a cheap material, such as carbon, is used as the conductive material, the production cost of an enzyme electrode can be decreased to a large extent and, thus, this method is especially advantageous for producing a disposable enzyme electrode.

As explained in detail below, when the enzyme electrode of the present invention is used for determining the concentration of ATP in a sample, a voltage is applied to the enzyme electrode between the working electrode thereof and the counter electrode thereof (or between the working electrode thereof and the reference electrode thereof). Therefore, the shapes of the electrodes are appropriately selected so that the electrodes can be connected to a means for applying the voltage through a conductor and the like.

If desired, an electric lead can be formed on the insulating substrate by using a conductive material which is different from that used for producing the electrodes, and a means for applying the voltage to the enzyme electrode can be connected to the electric lead through a conductor.

The electric lead can be formed by substantially the same method as described above in connection with the electrodes.

Further, if desired, an insulating layer may be formed on the electrode system (a) for maintaining the surface area of an exposed portion (i.e., the below-mentioned portion of an electrode which gets in contact with a sample solution) of each of the electrodes at a predetermined value and for preventing the occurrence of short-circuiting. In general, an electric insulating polymer, such as a thermosetting polyester, is used as a material for the insulating layer.

Figure 1C:
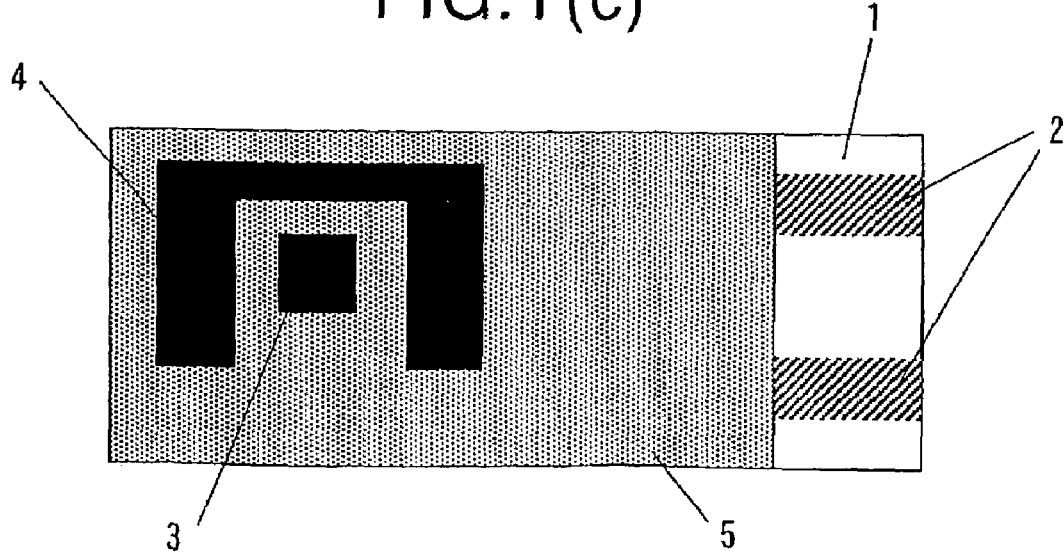
Figure 2:
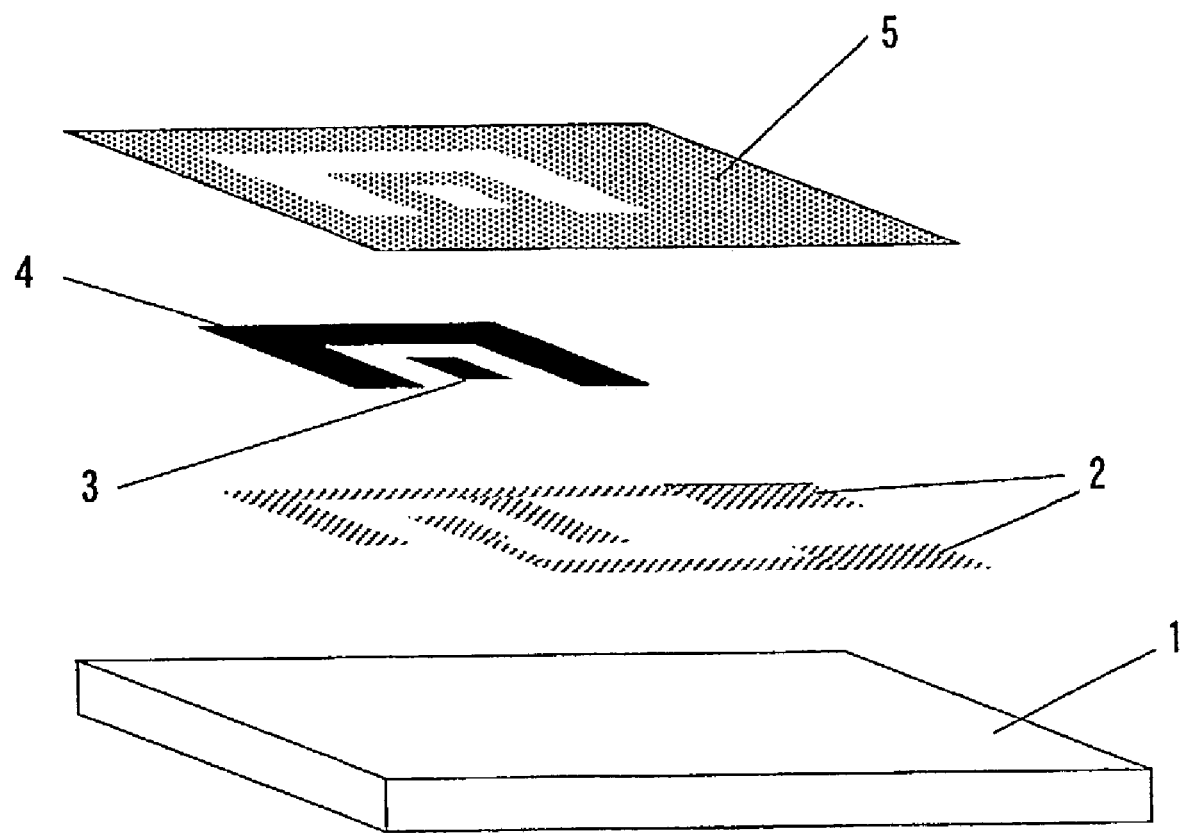
FIG. 2 is a schematic exploded diagram showing the relative positional relationships between the components constituting the electrode system used in Examples 1 and 2 and Reference Examples 2 to 4, wherein insulating substrate 1, electric leads 2,2, working electrode 3, counter electrode 4 and insulating layer 5 are exploded in the thickness-wise direction.

An example of shapes of the insulating layers is shown in FIGS. 1(c) and 2. As apparent from these drawings, in this example, the insulating layer is formed on electrode system (a) at its surface portions except those surface portions which correspond to the terminal portions of electric leads 2,2, whole portion of working electrode 3 and whole portion of counter electrode 4. The terminal portions of electric leads 2,2 are exposed without being covered with the insulating layer so that the electric leads can be connected to a conductor and the like which are used for connecting the means for applying the voltage to the enzyme electrode.

If desired, the electrodes may be subjected to surface treatment, such as washing, polishing and plasma etching.

For washing the surface of the electrode, use can be made of a method which uses an ultrasonic washing apparatus or a method which uses an appropriate detergent. Alternatively, these methods can be used in combination.

It is preferred that the above-mentioned detergent is a substance which does not damage the electrodes and the insulating substrate, and organic solvents and acids are generally used. As organic solvents, a polar solvent is preferred, and ketones (such as acetone) and alcohols (such as isopropyl alcohol) are especially preferred. As acids, diluted sulfuric acid is preferred.

In addition, an electrolytic cathode water can be used as the above-mentioned detergent. An electrolytic cathode water is an aqueous liquid which is formed on the side of a cathode when pure water or the like is subjected to electrolysis. The electrolytic cathode water exhibits the high ability to cause reduction although its pH is within the range of from neutral to weak alkali. Due to this property, the electrolytic cathode water can be preferably used as a detergent because it can give a negative charge to the surface of the insulating substrate and the surfaces of the particles attached thereto without causing damage on the insulating substrate and the electrodes, thereby preventing the particles, which have been detached from the surface of the substrate, from re-attaching to the substrate.

As methods for polishing the surface of the electrodes, there can be mentioned a method which uses an alumina suspension and a method which uses a non-woven fabric impregnated with a polar organic solvent, such as ethanol.

In the present invention, the surface treatment by plasma etching is preferred because it results in not only cleaning of the surfaces of the electrodes, but also improvement in the wetting properties of the surfaces of the electrodes. Improved wetting properties are advantageous for the below-mentioned immobilization of the enzymes.

Next, a detailed explanation is made on reaction layer (b).

As explained above, the reaction layer (b) used in the present invention comprises diaphorase (EC 1.6.99.2) (hereinafter, referred to as "DI"), 12α-hydroxysteroid dehydrogenase (EC 1.1.1.176) (hereinafter, referred to as "12α-HSD") and nicotinamide adenine dinucleotide synthetase (EC 6.3.1.5) (hereinafter, referred to as "NADS").

DI is an enzyme having the activity to catalyze the reduction of various compounds (especially, reduction of lipoacid derivatives into the corresponding dihydrolipoacid derivatives) by using nicotinamide adenine dinucleotide in the reduced state (NADH) as a coenzyme.

DI derived from various organisms, for example, mammals, such as calf and rat; yeasts; and bacteria, such as *Bacillus megaterium, Clostridium kluyveri, Bacillus stearothermophilus* and *Photobacterium fischeri*, are known in the art. In the present invention, DI derived from *Bacillus megaterium* is especially preferred.

12α-HSD is an enzyme having the activity to catalyze the oxidation of the hydroxyl group at the 12α-position of bile acids (and derivatives thereof) into a keto group by using nicotinamide adenine dinucleotide in the oxidized state ($NAD^+$) as a coenzyme.

12α-HSD derived from various organisms, for example, bacteria, such as *Bacillus sphaericus, Clostridium* sp. and *Eubacterium lentum*, are known in the art. In the present invention, 12α-HSD derived from *Bacillus sphaericus* is especially preferred.

NADS is an enzyme which catalyzes both of the hydrolysis of ATP into AMP and the synthesis of $NAD^+$ from nicotinic acid adenine dinucleotide (deamido-$NAD^+$) and ammonia and/or ammonium ion by using the energy released during the hydrolysis of ATP.

NADS derived from various organisms, for example, bacteria, such as *Bacillus stearothermophilus* and *Escherichia coli*, are known in the art. In the present invention, NADS derived from *Bacillus stearothermophilus* is especially preferred.

Among the conventional enzyme electrodes, many enzyme electrodes are known which employ a plurality of enzymes and which comprise a plurality of reaction layers, wherein the enzymes are separately contained in different reaction layers. Such enzyme electrodes have very complicated structures which require a complicated process for the production thereof. As a consequence, the production costs of these enzyme electrodes have been high.

On the other hand, in the enzyme electrode of the present invention, DI, 12α-HSD and NADS enzymes are contained in the same reaction layer. Therefore, the enzyme electrode of the present invention has a relatively simple structure and can be produced easily and at low cost.

There has been no conventional enzyme electrode containing DI, 12α-HSD and NADS enzymes in a single reaction layer. Each of Japanese Patent Application Laid-Open Specification Nos. Hei 6-88805 and Hei 9-229895 discloses an enzyme electrode having a reaction layer comprising three types of enzymes, wherein the reaction layer is formed on a working electrode. However, the enzyme electrodes disclosed in these patent documents are not designed for determining the concentration of ATP in a sample and, in addition, the enzymes of these enzyme electrodes do not contain any of DI, 12α-HSD and NADS.

In the present invention, with respect to the amounts of DI, 12α-HSD and NADS enzymes contained in the enzyme electrode, there is no particular limitation. However, from the viewpoint of improving the sensitivity of the enzyme electrode, with respect to the portion of the reaction layer which portion is superposed on the working electrode, it is preferred that the total amount of proteins is 2.5 mg or less per $cm^2$ of the superposed portion of the reaction layer, the amount of DI in terms of the activity thereof is 0.25 U or more per $cm^2$ of the superposed portion of the reaction layer, the amount of 12α-HSD in terms of the activity thereof is 0.63 U or more per $cm^2$ of the superposed portion of the reaction layer, and the amount of NADS in terms of the activity thereof is 0.063 U or more per $cm^2$ of the superposed portion of the reaction layer.

As explained in detail below, in order to determine the concentration of ATP in a sample by using the enzyme electrode of the present invention, ATP in a sample solution must diffuse into the reaction layer of the enzyme electrode and be hydrolyzed into AMP by NAPS in the reaction layer.

When the reaction layer contains a large amount of proteins, the rate at which ATP in the sample solution diffuses into the reaction layer becomes low (i.e., the amount of ATP diffusing into the reaction layer per unit time becomes decreased) and, as a result, a rapid analysis becomes difficult and the sensitivity of the enzyme electrode becomes low.

The sample solution which is subjected to the analysis by the enzyme electrode of the present invention has very low ATP concentration, that is micromolar (μM) ($10^{-6}$ M) level or less, generally nanomolar (nM) ($10^{-9}$ M) level, and, thus, the rate at which ATP in the sample solution diffuses into the reaction layer is intrinsically low. In addition, an operation for promoting the diffusion of ATP, such as agitation of the sample solution, is not conducted during the analysis using the enzyme electrode of the present invention and, hence, the proteins contained in the reaction layer markedly inhibit the diffusion of ATP.

Therefore, in the enzyme electrode of the present invention, with respect to the reaction layer, especially the portion thereof which is superposed on the working electrode, it is preferred that the total amount of proteins does not exceed the specific level defined in the present invention.

In the enzyme electrode of the present invention, with respect to the portion of the reaction layer which is superposed on the working electrode, the total amount of proteins is preferably 2.5 mg or less, more preferably 1.5 mg or less, most preferably 1.1 mg or less per $cm^2$ of the superposed portion of the reaction layer.

The total amount of proteins can be determined by taking out the reaction layer from the enzyme electrode and measuring the amount of proteins contained therein by conventional methods, for example colorimetric methods (such as a biuret method and a BCA method).

Each of Japanese Patent Application Laid-Open Specification Nos. Hei 6-88805 and Hei 9-229895 mentioned above (which discloses an enzyme electrode having a reaction layer comprising three types of enzymes which is formed on a working electrode) has a description on the minimum amounts of enzymes used, but has no description on the maximum amounts of the enzymes used.

Samples which are subjected to an analysis using the above-mentioned conventional enzyme electrodes have a relatively high concentration with respect to a target substance for analysis and, thus, the sensitivity required for in these conventional enzyme electrodes may be relatively low. This is considered to be one of the reasons why the adverse influences of the enzyme content on the sensitivity of the enzyme electrode were not taken into consideration in the conventional enzyme electrodes.

In addition, it should be noted that the high concentration of a target substance for analysis in a sample results in a relatively high diffusion rate of the target substance. In the case of the conventional enzyme electrodes, since the samples have high target substance concentrations, the lowering in the diffusion rate caused by the high enzyme concentration of the reaction layer and the accompanying lowering of the sensitivity were not considered to be a problem even when the analysis is conducted within a short time without agitating of the sample.

On the other hand, when the amount of the enzymes in the reaction layer is too small, the magnitude of electric signals which is proportional to the amount of ATP becomes too small, and the difference between the electric signals caused by ATP and the background noise becomes too small to be detected. As a result, the sensitivity of the enzyme electrode becomes low.

Therefore, in the enzyme electrode of the present invention, with respect to the reaction layer, especially the portion thereof which is superposed on the working electrode, it is preferred that each of the amounts of DI, 12α-HSD and NADS in terms of the activity thereof is not less than the specific level defined in the present invention.

In the enzyme electrode of the present invention, with respect to the portion of the reaction layer which is superposed on the working electrode, the amount of DI in terms of the activity thereof is preferably 0.25 U or more, more preferably 1.0 U or more, most preferably 2.5 U or more per $cm^2$ of the superposed portion of the reaction layer.

The enzyme activity of DI is defined as the molar amount of NADH which is oxidized per unit time by DI in the presence of an electron carrier (mentioned below) at 37° C. and pH 8.0. 1 U of DI corresponds to the enzyme activity of DI used to oxidize 1 μmol of NADH per minute.

In the above-mentioned reaction, oxidation of NADH occurs simultaneously with the reduction of the electron carrier and, thus, the molar amount of NADH oxidized is equivalent to the molar amount of the electron carrier in the reduced state which is generated by the reduction of the electron carrier. Thus, for the sake of convenience, the enzyme activity of DI is determined by measuring the molar amount of the reduced state electron carrier which is generated as a result of the enzyme reaction.

In the enzyme electrode of the present invention, with respect the portion of the reaction layer which is superposed on the working electrode, the amount of 12α-HSD in terms of the activity thereof is preferably 0.63 U or more, more preferably 2.5 U or more, most preferably 6.25 U or more per $cm^2$ of the superposed portion of the reaction layer.

The enzyme activity of 12α-HSD is defined as the molar amount of deoxycholic acid (a type of bile acid) which is oxidized per unit time by 12α-HSD at 37° C. and pH 8.0. 1 U of 12α-HSD corresponds to the enzyme activity of 12α-HSD used to oxidize 1 μmol of deoxycholic acid per minute.

During the above-mentioned reaction, oxidation of deoxycholic acid occurs simultaneously with the generation of NADH by the reduction of $NAD^+$ and, thus, the molar amount of the generated NADH is equivalent to the molar amount of deoxycholic acid oxidized. When the generated NADH is oxidized in the above-mentioned manner by DI in the presence of an electron carrier (mentioned below), the reduction of the electron carrier occurs simultaneously therewith and, thus, the molar amount of NADH oxidized is equivalent to the molar amount of the reduced state electron carrier which is generated by the reduction of the electron carrier.

The enzyme activity of 12α-HSD is determined as follows. Deoxycholic acid is oxidized by 12α-HSD in the presence of 200 U/ml of DI and an electron carrier to thereby generate NADH and, then, the oxidation of the generated NADH and the reduction of the electron carrier are catalyzed by DI. Subsequently, the molar amount of the resultant reduced state electron carrier is measured to thereby determine the enzyme activity of 12α-HSD.

In the enzyme electrode of the present invention, with respect the portion of the reaction layer which is superposed on the working electrode, the amount of NADS in terms of the activity thereof is preferably 0.063 U or more, more preferably 0.25 U or more, most preferably 0.625 U or more per $cm^2$ of the superposed portion of the reaction layer.

The enzyme activity of NADS is defined as the molar amount of $NAD^+$ synthesized per unit time by NADS at 37° C. and pH 9.5. 1 U of NADS corresponds to the enzyme activity of NADS used to synthesize 1 μmol of $NAD^+$ per minute.

The enzyme activity of NADS is determined as follows. $NAD^+$ is synthesized by NADS in the presence of 200 U/ml of 3α-hydroxysteroid dehydrogenase and the synthesized $NAD^+$ is reduced by 3α-hydroxysteroid dehydrogenase to thereby generate NADH. Subsequently, the amount of the generated NADH is determined by measuring the absorbance at 340 nm, thereby determining the enzyme activity of NADS.

The enzyme electrode of the present invention may contain proteins other than the above-mentioned three enzymes as long as the proteins cause no adverse influence on the performance of the enzyme electrode. For example, bovine serum albumin, 3α-hydroxysteroid dehydrogenase, 7α-hydroxysteroid dehydrogenase, alcohol dehydrogenase and glucose dehydrogenase, may be contained in the reaction layer of the enzyme electrode.

The enzyme electrode of the present invention is designed so that at least a portion of the reaction layer is superposed on the working electrode, wherein DI, 12α-HSD and NADS enzymes contained in the superposed portion of the reaction layer are immobilized on the surface of the working electrode, so that a compound generated in the reaction layer can reach the surface of the working electrode.

Hereinbelow, methods for forming the above-mentioned reaction layer (b) is explained in detail.

With respect to the methods for forming the reaction layer, there is no particular limitation as long as a uniform coating containing DI, 12α-HSD and NADS enzymes is formed. In general, the formation of the reaction layer also serves to immobilize DI, 12α-HSD and NADS enzymes on the surface of the working electrode.

The immobilization of the enzymes on the surface of the working electrode encompasses not only the immobilization performed by directly binding the enzymes to the surface of the working electrode, but also the immobilization which is achieved without directly binding the enzymes to the surface of the working electrode.

With respect to the methods for forming the reaction layer (the methods for immobilizing the enzymes), use can be made of the conventional methods, such as those exemplified below:

(1) a method in which DI, 12α-HSD and NADS are directly immobilized on the surface of the working electrode by using a crosslinking agent, such as glutaraldehyde;

(2) a method in which a coating having an appropriate functional group at the surface thereof is formed on the surface of the working electrode, and DI, 12α-HSD and NADS are bound to the functional groups either directly or by using a crosslinking agent;

(3) a method in which a hydrophilic polymer layer is superposed on the surface of the working electrode, and an aqueous solution containing DI, 12α-HSD and NADS is dropwise added onto the hydrophilic polymer layer, followed by drying; and (4) a method in which a polymer having a network structure (e.g., crosslinked albumin) is coated on the surface of the working electrode, and DI, 12α-HSD and NADS are incorporated into the coating.

Specific examples of coatings used in method (2) above include a coating having amino groups on the surface thereof which is prepared by a plasma polymerization of a monomer containing nitrogen atoms, and a coating prepared by spin coating and drying a solution of a silane coupling agent having a functional group (such as aminosilanes, vinylsilanes or epoxysilanes). When a silane coupling agent coating is used, from viewpoints of the adhesiveness of such coating with the working electrode and the selective permeability of the substances which participate in the analysis of ATP, it is preferred that the silane coupling agent is γ-aminopropyltriethoxysilane (which is one of aminosilanes). In this case, the concentration of the silane coupling agent in the solution used for preparing the coating is preferably about 1% (v/v).

The above-mentioned method (3) is preferred from a viewpoint of the prevention of unnecessary interactions between proteins and the electrode system, such as binding of proteins to the electrode system.

The hydrophilic polymer layer is preferably formed by coating the surface of the working electrode with a 0.05 to 2% (w/w) aqueous solution of a hydrophilic polymer, followed by drying.

Examples of hydrophilic polymers include water soluble cellulose derivatives, such as carboxymethylcellulose, hydroxyethylcellulose, hydroxypropylcellulose, carboxyethylmethylcellulose and ethylcellulose; polyvinyl pyrrolidone; polyviny alcohol; gelatin and derivatives thereof; polyacrylic acids and salts thereof; starch and derivatives thereof; polymers of maleic acid anhydrate and salts thereof; polyacrylamide; methacrylate resin; and poly-2-hydroxyethyl methacrylate.

With respect to the methods for applying an enzyme solution to the surface of the working electrode, use can be made of a dropping method, a spin coating method and a dipping method (a dip coating method), and the spin coating method which is capable of precisely controlling the thickness of a coating is preferred.

It is preferred that the enzyme solution is dried at a temperature which does not cause denaturation of the enzyme activities, that is, a temperature in the range of from room temperature (25° C.) to 40° C. The time needed for drying the enzyme solution varies depending on the temperature, but it is generally in the range of from 0.5 to 24 hours. The drying can be conducted in air, but alternatively, drying can be conducted under an atmosphere of inert gas, such as nitrogen gas. For example, use can be made of a nitrogen blow method in which the enzymes are dried by blowing nitrogen gas onto the substrate.

By the use of the enzyme electrode obtained in the above-mentioned manner, it has become possible to conduct a determination of the ATP concentration of a sample easily and rapidly, with high sensitivity, without the need of a cumbersome pretreatment.

Hereinbelow, the method for determining the concentration of ATP in a sample by using the enzyme electrode of the present invention is explained in detail.

In the present invention, the concentration of ATP in a sample is determined by a method which comprises:

mixing a sample with an aqueous solution containing nicotinic acid adenine dinucleotide (deamido-NAD$^+$), a bile salt, an electron carrier and at least one member selected from the group consisting of ammonia and ammonium ion, to thereby obtain a sample solution;

contacting the sample solution with the working electrode, counter electrode and optionally reference electrode of the above-mentioned enzyme electrode, to thereby form an electric circuit through the sample solution;

measuring the electric current at the working electrode while applying a voltage to the enzyme electrode between the working electrode thereof and the counter electrode thereof or between the working electrode thereof and the reference electrode thereof to thereby perform an oxidation reaction of the electron carrier on the surface of the working electrode, wherein when the enzyme electrode does not contain a reference electrode, the voltage is applied between the working electrode and the counter electrode and wherein when the enzyme electrode contains a reference electrode, the voltage is applied between the working electrode and the reference electrode; and calculating the amount of ATP, based on the measured value of the electric current at the working electrode.

At least one member selected from the group consisting of ammonia and ammonium ion is a substrate for NADS. In general, the concentration of ammonia and/or ammonium ion in a sample solution is adjusted to 2 mM to 200 mM by adding either an aqueous ammonia or an inorganic or organic ammonium salt to the sample solution.

Deamido-NAD$^+$ is also a substrate for NADS. In general, the concentration of deamido-NAD$^+$ in the sample solution is 2 μM to 2 mM.

A bile salt is a substrate for 12α-HSD, and use can be made of salts of bile acids having a hydroxyl group at the 12α-position thereof, such as sodium salts and potassium salts of cholic acid, deoxycholic acid and the like. In general, the concentration of the bile salt in the sample solution is 0.2 mM to 20 mM.

The electron carrier is a substrate for DI, and it may take two different states, namely an oxidized state and a reduced state. An electron carrier in the oxidized state is reduced by DI in the presence of nicotin amide adenine dinucleotide (NAD$^+$) and is converted into the reduced state. When a sufficient amount of voltage is applied to the enzyme electrode, wherein when the enzyme electrode does not contain a reference electrode, the voltage is applied between the working electrode and the counter electrode and wherein when the enzyme electrode contains a reference electrode, the voltage is applied between the working electrode and the reference electrode, the electron carrier in the reduced state is oxidized electrochemically at the surface of the working electrode and supplies electrons to the working electrode while the reduced state electron carrier is converted into the oxidized state. The voltage sufficient to oxidize an electron carrier varies depending on the type of the electron carrier, but it is generally in the range of from 100 mV to 600 mV.

Examples of electron carriers include ferricyanide complexes, such as potassium ferricyanide and sodium ferricyanide; quinones, such as 1,4-benzoquinone, toluquinone, 1,4-naphtoquinone, vitamin K$_3$, 2,5-dichloro-benzoquinone, duroquinone, 2,5-dimethylbenzoquinone and 2,6-dimethylbenzoquinone; flavins, such as riboflavin, flavin mononucleotide and flavin adenine dinucleotide; phenols, such as 4-aminophenol, 4-methylaminophenol, 2,6-dichlorophenol and indophenol; phenazonium derivatives, such as phenazine sulfate; phenothiazinium derivatives, such as methylene blue; ferrocenes, such as hydroxymethylferrocene, 1-hydroxyethylferrocene, ferrocenium hexafluorophosphate and ferrocenium tetrafluoroborate; phenylene diamines, such as N,N,N',N'-tetramethylphenylene diamine. Among these compounds, ferricyanide complexes and ferrocenes are preferred.

These electron carriers can be used individually or in combination. In general, the concentration of the electron carrier in the sample solution is from 0.1 mM to 100 mM.

Further, in order to ensure that each of DI, 12α-HSD and NADS enzymes in the reaction layer exhibits a satisfactory level of the enzyme activity, a buffering agent is preferably added to the above-mentioned sample solution.

Examples of buffering agents include glycine, phosphoric acid, acetic acid, boric acid, citric acid, phthalic acid and salts (including hydrogen salts) thereof. In addition, the reagents used for preparing the so-called "Good's buffer", such as CAPSO and CHES, can be also used.

These buffering agents can be used individually or in combination.

The type and amount of the buffering agent are appropriately selected based mainly on the optimal pH of DI, 12α-HSD and NADS enzymes so that each of DI, 12α-HSD and NADS enzymes exhibits a satisfactory level of enzyme activity. However, depending on the type of the buffering agent, the influence of the buffering agent on the reaction layer (for example, the occurrence of inadvertent side reactions) should also be taken into consideration.

The pH which is achieved by the use of the buffering agent is preferably in the range of from 6.0 to 10.0, more preferably 8.0 to 9.5. The concentration of the buffering agent in the sample solution is preferably from 10 mM to 1,000 mM, more preferably from 25 mM to 400 mM.

If desired, the sample solution may contain reagents other than those mentioned above, such as salts and surfactants.

With respect to the properties of the reagents used in the present invention and a method for mixing the sample with an aqueous solution containing the reagents, there is no particular limitation. For example, use can be made of a method in which a reagent in a solid (dried) form is immobilized at an appropriate position of the enzyme electrode so that the immobilized reagent dissolves into the sample when the sample gets in contact with the enzyme electrode.

When the above mentioned sample solution gets in contact with the enzyme electrode, the sample solution infiltrates into at least a portion of the reaction layer formed on the working electrode, and NADS in the reaction layer synthesizes the oxidized state nicotinamide adenine dinucleotide (NAD$^+$) from deamido-NAD$^+$ and ammonia and/or ammonium ion in the sample solution, wherein the amount of synthesized NAD$^+$ is proportional to the ATP concentration of the sample solution. The synthesized NAD$^+$ is detected by the enzymatic cycling which uses the combination of 12α-HSD and DI.

12α-HSD generates the reduced state nicotinamide adenine dinucleotide (NADH) from the above-synthesized NAD⁺ and simultaneously oxidizes the bile salt in the sample solution.

DI regenerates NAD⁺ from the generated NADH and simultaneously reduces the electron carrier in the oxidized state, to thereby convert the electron carrier into the reduced state.

At this point, when a voltage which is sufficient to perform an oxidation reaction of the electron carrier is applied to the enzyme electrode between the working electrode thereof and the counter electrode thereof (when the enzyme electrode does not contain a reference electrode) or between the working electrode thereof and the reference electrode thereof (when the enzyme electrode contains a reference electrode), as explained above, the reduced state electron carrier is oxidized electrochemically on the surface of the working electrode and supplies the electrons to the working electrode, thereby regenerating the oxidized state electron carrier.

As explained above, an oxidation of NADH/reduction of NAD⁺ and an oxidation/reduction of electron carrier are repeatedly performed in the enzyme electrode. During the repetition of these reactions, electrons are continuously supplied to the working electrode in accordance with the electrochemical oxidation of the reduced state electron carriers on the surface of the working electrode.

The rate at which the electrons are supplied to the working electrode, namely the value of electric current flowing through the working electrode, is proportional to the ATP concentration of the sample solution and, thus, the ATP concentration of the sample solution can be determined by measuring the electric current at the working electrode.

Illustratively stated, the concentration of ATP in a sample can be easily determined by a process in which a calibration curve showing the correlation between the ATP concentration and the value of electric current at the working electrode is prepared using standard solutions having known ATP concentrations, and a sample having unknown ATP concentration is subjected to analysis with the enzyme electrode of the present invention so as to measure the electric current at the working electrode, and the amount of ATP is easily calculated from the measured value of the electric current by using the above-mentioned calibration curve.

In the enzymatic cycling of NAD⁺/NADH system which is performed using the combination of DI and 12α-HSD, the number of the reactions conducted per unit time is large (i.e., the rate of the enzymatic cycling is high) and thus, the value of electric current flowing through the working electrode, relative to a unit amount of ATP, is large. As a result, the enzyme electrode of the present invention exhibits high sensitivity and it enables a rapid analysis.

In the present invention, the voltage is generally applied to the enzyme electrode for 0.5 to 2 minutes.

It should be noted that the enzyme electrode of the present invention is used mainly for the quantitative analysis of ATP, but it can be also used for the quantitative analysis of deamido-NAD⁺ and quantitative analysis of ammonia and/or ammonium ion.

The quantitative analysis of deamido-NAD⁺ is performed in substantially the same manner as in the above-mentioned determination of the ATP concentration except that ATP is used in place of deamido-NAD⁺. The quantitative analysis of ammonia and/or ammonium ion is performed in substantially the same manner as in the above-mentioned determination of the ATP concentration except that ATP is used in place of ammonia and/or ammonium ion.

A method comprising the steps of generating NAD⁺ in an amount which is proportional to the amount of ATP in a sample and determining the concentration of ATP by using the enzymatic cycling of the NAD⁺/NADH system has been known in the art (see Japanese Patent Application Laid-Open Specification No. Hei 8-336397). However, in this method, the ATP concentration is determined by using the coloration of tetrazolium salt, namely by an optical technique and, thus, this prior art has no teaching about an enzyme electrode. Further, in this method, the enzymatic cycling is conducted without using the combination of DI and 12α-HSD, and this patent document has no suggestion about the use of DI and 12αHSD in combination.

In addition, an enzymatic cycling of the NAD⁺/NADH system by the combination of DI and 12α-HSD in the reaction layer formed on an electrode has been conventionally known, and an enzyme electrode which employs such an enzymatic cycling has been disclosed in prior art (see Japanese Patent Application Laid-Open Specification No. 2000-189188). However, this enzyme electrode is designed only for the analysis of NAD⁺/NADH and has no teaching about the conducting of other reactions for generating NAD⁺/NADH in the vicinity of the electrodes.

The determination of the ATP concentration by using the enzyme electrode of the present invention can be performed by using a system comprising:

the above-mentioned enzyme electrode;

means for applying a voltage to the above-mentioned enzyme electrode between the working electrode thereof and the counter electrode thereof or between the working electrode thereof and the reference electrode thereof, the voltage being sufficient to perform an oxidation reaction of the electron carrier on the surface of the working electrode; and means for measuring the electric current at the working electrode.

With respect to the means for applying voltage and means for measuring the electric current, various means are known in the art, and use can be made of appropriate conventional means. The means for applying voltage and the means for measuring the electric current may comprise either two separate apparatuses or a single apparatus having both a function to apply voltage and a function to measure the electric current.

The enzyme electrode of the present invention has been designed so as to enable the use thereof as a disposable enzyme electrode and, thus, with respect to the system comprising the enzyme electrode, it is preferred that the exchange of the enzyme electrode can be performed with ease. Therefore, it is preferred that the above-mentioned system of the present invention has a structure which enables the enzyme electrode to be attached to and detached from the system with ease. Examples of such structures include:

a structure in which only the enzyme electrode is capable of being attached and detached; and a structure in which a part of the system comprising the enzyme electrode and other components (for example, wires for connecting the enzyme electrode to other components of the system) is capable of being attached and detached.

In addition, it is preferred that the above-mentioned system further comprises means for calculating the amount of ATP, based on the measured value of the electric current at the working electrode.

As the calculation means, various data processing apparatuses are known in the art, and these apparatuses convert the measured value of the electric current into analogue or digital electric signals and process the electric signals by a calculator and the like so as to calculate the amount (concentration) of ATP. The amount (concentration) of ATP can be determined very easily by using such means.

BEST MODE FOR CARRYING OUT THE INVENTION

Hereinbelow, the present invention will be described in more detail with reference to the following Examples and Reference Examples, but they should not be construed as limiting the scope of the present invention.

REFERENCE EXAMPLE 1

An experiment was performed to confirm that a reaction layer comprising diaphorase (DI), 12α-hydroxysteroid dehydrogenase (12α-HSD) and nicotinamide adenine dinucleotide synthetase (NADS) can be used as a reaction layer of an enzyme electrode for determining the concentration of adenosine triphosphate (ATP).

A 25% (w/v) aqueous trehalose solution containing 3,200 U/ml of DI (catalogue no. T-06, manufactured and sold by Asahi Kasei Corporation, Japan), 9,600 U/ml of 12α-HSD (catalogue no. T-29, manufactured and sold by Asahi Kasei Corporation, Japan) and 880 U/ml of NADS (catalogue no. T-67, manufactured and sold by Asahi Kasei Corporation, Japan) was prepared and 0.5 μl of the prepared aqueous trehalose solution containing DI, 12α-HSD and NADS enzymes was mixed with 0.25 μl of a 1% (v/v) aqueous glutaraldehyde solution to thereby obtain a mixture. A mirror-finished, glassy carbon electrode having a diameter of 3 mm (catalogue no. 11-2012, manufactured and sold by BAS Inc., Japan) was coated with the obtained mixture and the resultant carbon electrode was allowed to stand still at room temperature (25° C.) for 2 hours, to thereby immobilize the enzymes on the surface of the carbon electrode. As a result, a reaction layer containing DI, 12α-HSD and NADS enzymes was formed on the surface of the above-mentioned carbon electrode. The total amount of protein was 1.16 mg per $cm^2$ of the reaction layer, and the amounts of DI, 12α-HSD and NADS in terms of activities thereof were, respectively, 22.6 U, 67.9 U and 6.2 U per $cm^2$ of the reaction layer.

The thus prepared carbon electrode (as a working electrode) was attached to MCA Microcell Kit (catalogue no. 11-1065, manufactured and sold by BAS Inc., Japan), together with a saturated calomel electrode (catalogue no. 11-2055, manufactured and sold by BAS Inc., Japan) (as a reference electrode) and a platinum electrode (catalogue no. 11-2230, manufactured and sold by BAS Inc., Japan) (as a counter electrode). The MCA Microcell Kit having attached thereto these three electrodes were connected to BAS-100B-type potentiostat (manufactured and sold by BAS Inc., Japan) (the potentiostat has a function of an ammeter for measuring the electric current at the working electrode), thereby obtaining a system for measuring the ATP concentration.

On the other hand, standard solutions 1 to 5 as mentioned below were prepared:

| | |
|---|---|
| Standard solution 1: | 0.1 M phosphate buffer (pH 8.5) containing 2 mM sodium deoxycholate, 5 mM magnesium chloride, 20 mM ammonium chloride and 0.1 mM hydroxymethylferrocene; |
| Standard solution 2: | Standard solution 1 modified so as to further contain 2 mM of nicotinic acid adenine dinucleotide (deamido-$NAD^+$); and |
| Standard solutions 3 to 5: | Standard solution 2 modified so as to further contain ATP, wherein standard solutions 3, 4 and 5 contain 0.2 μM, 0.5 μM and 1 μM of ATP, respectively. |

A sample holder (catalogue no. 11-2228, manufactured and sold by BAS Inc., Japan) was attached to the above-mentioned MCA Microcell Kit, and 200 μl of standard solution 1 was injected into the sample holder. The above-mentioned working electrode was immersed in standard solution 1 and a voltage of 0.2 V was applied between the working electrode and the reference electrode at 30° C. for 30 minutes.

The same operation as mentioned above was repeated, except that standard solution 2 was used in place of standard solution 1. A voltage of 0.2 V was applied between the working electrode and the reference electrode at 30° C. for 10 minutes and the electric current at the working electrode was measured by means of the above-mentioned potentiostat.

Subsequently, the same operation as conducted above for measuring the electric current with respect to standard solution 2 was repeated, except that each of standard solutions 3 to 5 was individually used in place of standard solution 2.

In addition, the same operation as conducted above for measuring the electric current with respect to standard solution 2 was repeated, except that water was used in place of standard solution 2 (this measurement is referred to as a "blank test").

The value of electric current obtained in the blank test was subtracted from each of the electric current values obtained with respect to standard solutions 2 to 5, so as to obtain corrected electric current values. The corrected electric current values of standard solutions 2 to 5 were 150 nA, 391 nA, 503 nA and 735 nA, respectively.

Figure 3:
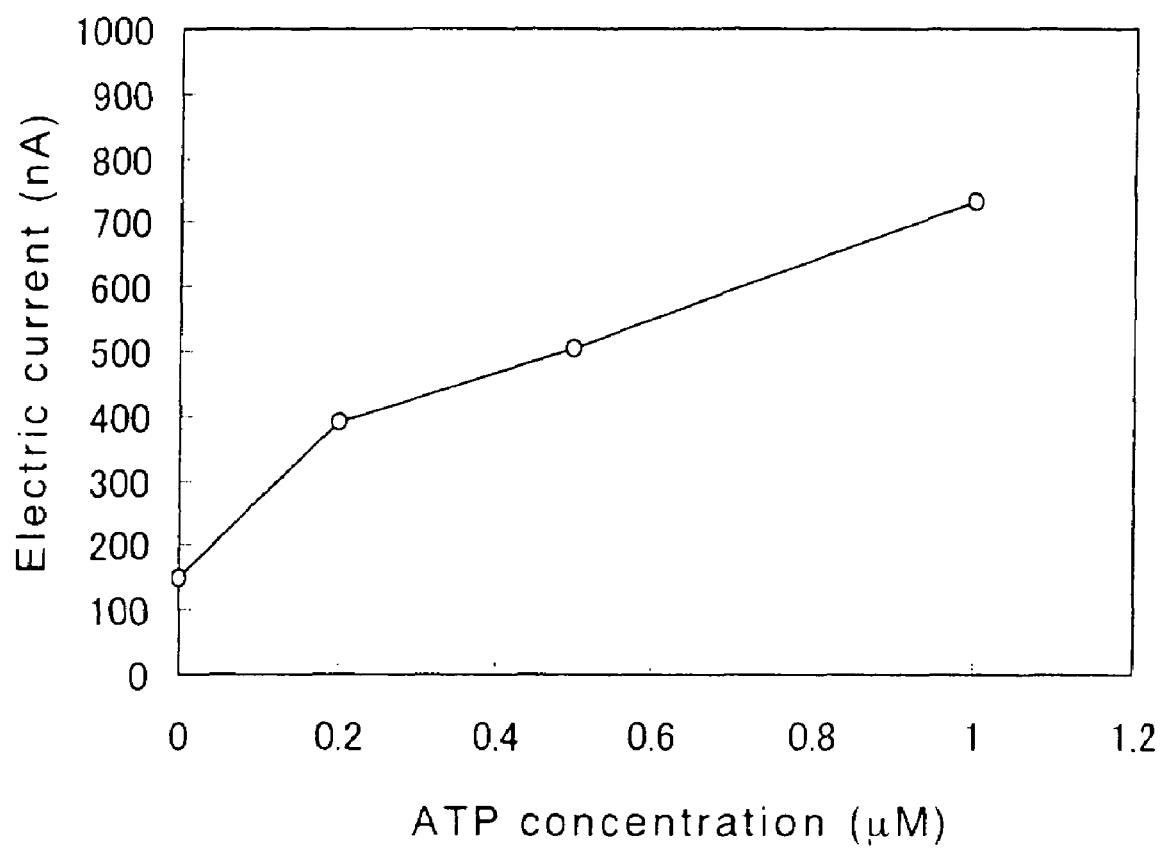
FIG. 3 is a graph showing the correlation between the ATP concentrations of the samples analyzed in Reference Example 1 and the electric current values obtained with respect to the samples.

The correlation between the corrected electric current values and the ATP concentrations of standard solutions 2 to 5 is shown in FIG. 3.

As shown in FIG. 3, in the system obtained above, the value of electric current flowing through the working electrode was proportional to the ATP concentration of a sample and, hence, the ATP concentration of a sample can be calculated from the measured value of the electric current. From this result, it was confirmed that a reaction layer comprising DI, 12α-HSD and NADS enzymes can be used as a reaction layer for an enzyme electrode for determining the concentration of ATP.

EXAMPLE 1

An electrode system which comprises insulating layer 5 shown in FIG. 1(*c*) was prepared by screen printing.

A PET film having a thickness of 188 μm (trade name: Melinex S, manufactured and sold by Du Pont Co. Ltd., Japan) was used as insulating substrate 1. Electric leads 2, 2 were formed on insulating substrate 1 by screen printing using a silver paste (catalogue no. FA-353, manufactured and sold by Fujikura Kasei Co., Ltd., Japan) and a resist (catalogue no. XC-101G, manufactured and sold by Fujikura Kasei Co., Ltd., Japan) (see FIG. 1(a)).

Next, working electrode 3 and counter electrode 4 were, respectively, formed in association with electric leads 2,2 by screen printing using a carbon paste (catalogue no. FC-415, manufactured and sold by Fujikura Kasei Co., Ltd., Japan) and the above-mentioned resist, to thereby obtain an electrode system precursor (see FIG. 1(b)). The shape of working electrode 3 was a square of 4 mm×4 mm.

On the thus obtained electrode system precursor at its surface portion except those surface portions which correspond to the terminal portions of electric leads 2,2, the whole portion of working electrode 3 and the whole portion of counter electrode 4, a thermosetting polyester coating was formed as insulting layer 5, to thereby obtain an electrode system (see FIG. 1(c)).

Subsequently, the surface of working electrode 3 of the obtained electrode system was polished using an aqueous alumina suspension.

5 μl of a 25% (w/v) aqueous trehalose solution containing DI, 12α-HSD and NADS enzymes, which solution is the same as used in Reference Example 1, was mixed with 2.5 μl of a 1% (v/v) aqueous glutaraldehyde solution to thereby obtain a mixture. The obtained mixture was coated on the working electrode of the above-obtained electrode system and the resultant entire electrode system was allowed to stand still at room temperature (25° C.) for 2 hours, to thereby immobilize the enzymes on the surface of the working electrode. As a result, an enzyme electrode having a reaction layer, containing DI, 12α-HSD and NADS enzymes, formed on the working electrode of the electrode system was obtained. The shape of the reaction layer was a square of 6 mm×6 mm, and the reaction layer covered the whole portion of the working electrode. The total amount of protein was 2.15 mg per $cm^2$ of the reaction layer, and the amounts of DI, 12α-HSD and NADS in terms of activities thereof were, respectively, 44.4 U, 133.3 U and 12.2 U per $cm^2$ of the reaction layer.

The working electrode and the counter electrode of this enzyme electrode were connected to a potentiostat which was the same as used in Reference Example 1.

On the other hand, standard solutions 6 to 11 as mentioned below were prepared:

| | |
|---|---|
| Standard solution 6: | 0.1 M phosphate buffer (pH 8.5) containing 2 mM sodium deoxycholate, 5 mM magnesium chloride, 20 mM ammonium chloride and 10 mM potassium ferricyanide; |
| Standard solution 7: | Standard solution 6 modified so as to further contain 2 mM of deamido-$NAD^+$; and |
| Standard solutions 8 to 11: | Standard solution 7 modified so as to further contain ATP, wherein standard solutions 8, 9, 10 and 11 contain 0.1 μM, 0.2 μM, 0.4 μM and 1 μM of ATP, respectively. |

Standard solution 6 was dropped on the working electrode of the above-obtained enzyme electrode until the whole surface of the working electrode was wetted with standard solution 6. Then, a voltage of 0.2 V was applied between the working electrode and the counter electrode at 22° C. for 30 minutes.

The same operation as mentioned above was repeated, except that standard solution 7 was used in place of standard solution 6. A voltage of 0.2 V was applied between the working electrode and the counter electrode at 22° C. for 10 minutes and the electric current at the working electrode was measured by means of the potentiostat.

Subsequently, the same operation as conducted above for measuring the electric current with respect to standard solution 7 was repeated, except that each of standard solutions 8 to 11 was individually used in place of standard solution 7.

In addition, the same operation as conducted above for measuring the electric current with respect to standard solution 7 was repeated, except that water was used in place of standard solution 7 (this measurement is referred to as a "blank test").

The value of electric current obtained in the blank test was subtracted from each of the electric current values obtained with respect to standard solutions 7 to 11, so as to obtain corrected electric current values. The corrected electric current values of standard solutions 7 to 11 were 173 nA, 290 nA, 413 nA, 594 nA and 791 nA, respectively.

Figure 4:
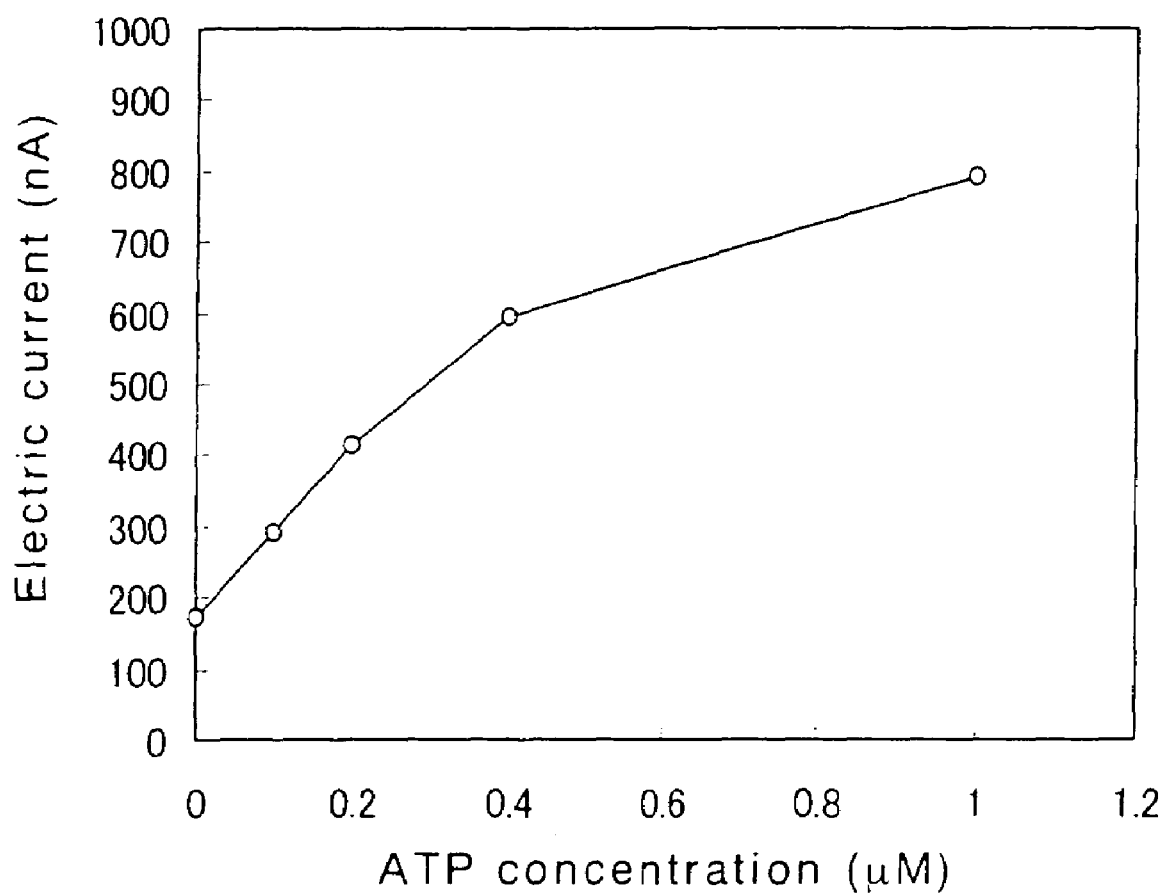
FIG. 4 is a graph showing the correlation between the ATP concentrations of the samples analyzed in Example 1 and the electric current values obtained with respect to the samples.

The correlation between the corrected electric current values and the ATP concentrations of standard solutions 7 to 11 is shown in FIG. 4.

As shown in FIG. 4, in the system prepared above, the value of electric current at the working electrode was proportional to the ATP concentration of a sample and, hence, the ATP concentration of a sample can be calculated from the measured value of the electric current.

EXAMPLE 2

An electrode system was prepared in substantially the same manner as in Example 1 except that the shape of the reaction layer was changed to a square of 4 mm×4 mm (thus, the surface area of the reaction layer was the same as that of the working electrode, namely 0.16 $cm^2$).

3 μl of a 0.5% (w/v) aqueous carboxymethylcellulose (CMC) solution was dropped on the working electrode of the above-mentioned electrode system, followed by drying, to thereby form a CMC layer on the working electrode of the electrode system.

6 μl of an aqueous solution containing 2.1 mg/ml (100 U/ml) of DI (which is the same as used in Reference Example 1), 4.6 mg/ml (1,000 U/ml) of 12α-HSD (which is same as used in Reference Example 1), 1.5 mg/ml (50 U/ml) of NADS (which is the same as used in Reference Example 1) and 2.5 mg/ml of bovine serum albumin (BSA) was dropped on the CMC layer, followed by drying, to thereby immobilize the enzymes contained in the solution on the surface of the working electrode. As a result, an enzyme electrode having a reaction layer, containing DI, 12α-HSD and NADS enzymes, formed on the working electrode was obtained. The total amount of protein was 0.40 mg per $cm^2$ of the reaction layer, and the amounts of DI, 12α-HSD and NADS in terms of activities thereof were, respectively, 3.75 U, 37.5 U and 1.875 U per $cm^2$ of the reaction layer.

The working electrode and the counter electrode of this enzyme electrode were connected to a potentiostat which was the same as used in Reference Example 1.

On the other hand, standard solutions 12 to 17 as mentioned below were prepared:

| | |
|---|---|
| Standard solution 12: | 0.1 M glycine buffer (pH 9.5) containing 2 mM sodium deoxycholate, 5 mM magnesium chloride, 20 mM ammonium chloride, 20 μM |

| | |
|---|---|
| | -continued |
| | deamido-NAD$^+$ and 10 mM potassium ferricyanide; and |
| Standard solutions 13 to 17: | Standard solution 12 modified so as to further contain ATP, wherein standard solutions 13, 14, 15, 16 and 17 contain 5 nM, 10 nM, 20 nM, 40 nM and 80 nM of ATP, respectively. |

100 μl of standard solution 12 was dropped on the working electrode of the above-obtained enzyme electrode until the whole surface of the electrode was wetted with standard solution 12. Then, a voltage of 400 mV was applied between the working electrode and the counter electrode at 25° C. for 30 seconds and the electric current at the working electrode was measured by means of the potentiostat (this measurement is referred to as a "blank test").

Subsequently, the same operation as conducted above for measuring the electric current with respect to standard solution 12 was repeated, except that each of standard solutions 13 to 17 was individually used in place of standard solution 12.

The value of electric current obtained in the blank test was subtracted from each of the electric current values obtained with respect to standard solutions 13 to 17, so as to obtain corrected electric current values. The corrected electric current values of standard solutions 13 to 17 were 39 nA, 73 nA, 154 nA, 301 nA and 753 nA, respectively.

Figure 5:
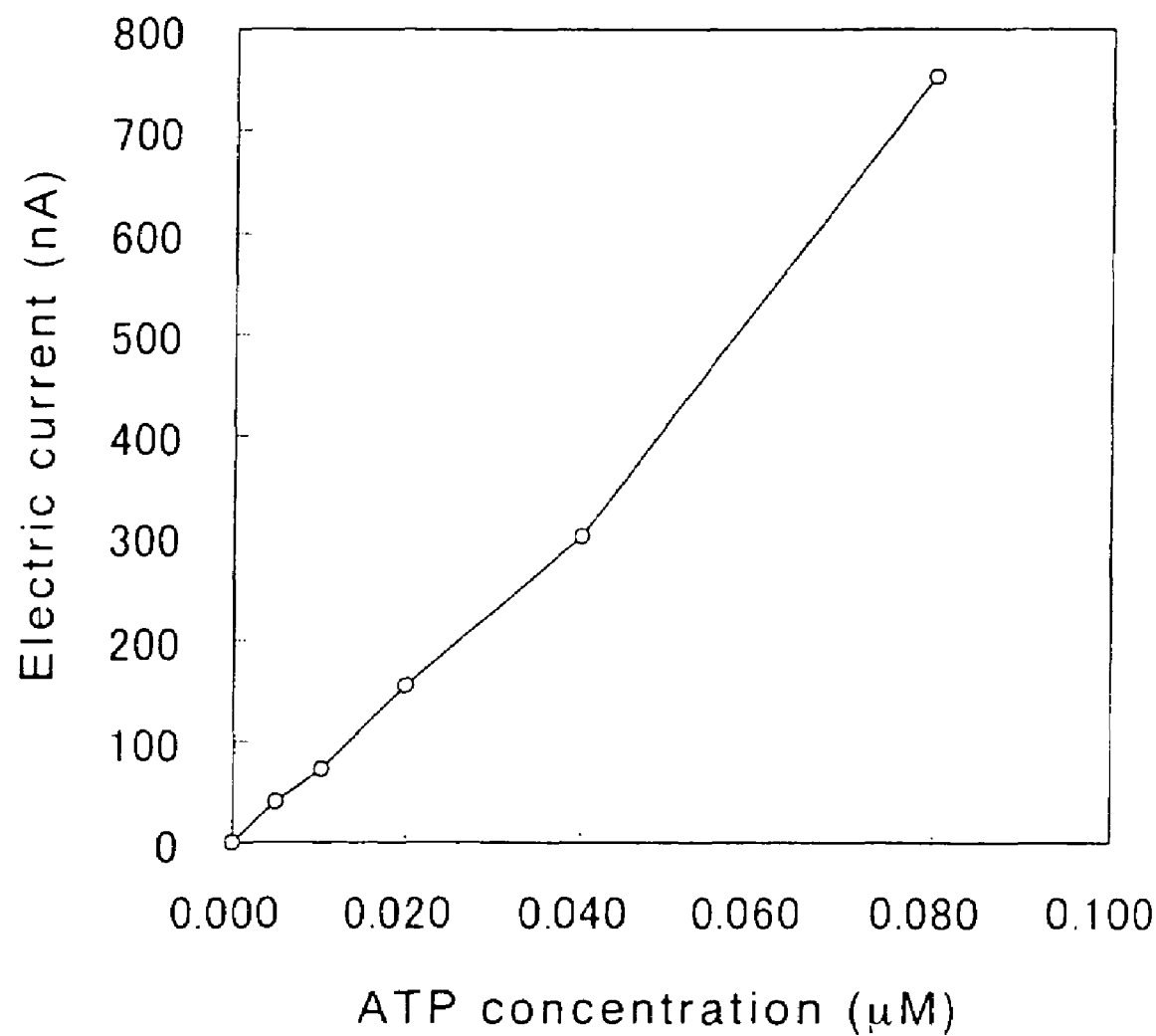
FIG. 5 is a graph showing the correlation between the ATP concentration of the samples analyzed in Example 2 and the electric current values obtained with respect to the samples.

The correlation between the corrected electric current values and the ATP concentrations of standard solutions 12 to 17 is shown in FIG. 5.

As shown in FIG. 5, in the system prepared above, the value of an electric current at the working electrode was proportional to the ATP concentration of a sample and, hence, the ATP concentration of a sample can be calculated from the measured value of the electric current.

REFERENCE EXAMPLE 2

The effect of the total amount of proteins on the sensitivity of the enzyme electrode was examined with respect to a portion of the reaction layer which is superposed on the working electrode.

Test (A):

An enzyme electrode was prepared in substantially the same manner as in Example 2, except that an aqueous solution containing 12.4 mg/ml (530 U/ml) of DI (which is the same as used in Reference Example 1), 5.9 mg/ml (1,300 U/ml) of 12α-HSD (which is the same as used in Reference Example 1) and 5.9 mg/ml (130 U/ml) of NADS (which is the same as used in Reference Example 1) was applied to the CMC layer to thereby form a reaction layer. The total amount of protein was 0.91 mg per cm$^2$ of the reaction layer, and the amounts of DI, 12α-HSD and NADS in terms of activities thereof were, respectively, 20 U, 50 U and 5 U per cm$^2$ of the reaction layer.

Using the thus prepared enzyme electrode, the same operations as conducted in Example 2 for measuring the electric currents were repeated, except that standard solution 18 was used in place of standard solutions 13 to 17. Standard solution 18 is standard solution 12 modified to further contain 500 nM of ATP.

Test (B):

An enzyme electrode was prepared in substantially the same manner as in Test (A) above, except that an aqueous solution containing 15.5 mg/ml (670 U/ml) of DI (which is the same as used in Reference Example 1), 7.4 mg/ml (1,700 U/ml) of 12α-HSD (which is the same as used in Reference Example 1) and 7.4 mg/ml (170 U/ml) of NADS (which is the same as used in Reference Example 1) was applied to the CMC layer to thereby form a reaction layer. The total amount of protein was 1.14 mg per cm$^2$ of the reaction layer, and the amounts of DI, 12α-HSD and NADS in terms of activities thereof were, respectively, 25 U, 62.5 U and 6.25 U per cm$^2$ of the reaction layer.

Using the thus prepared enzyme electrode, the same operations as conducted in Test (A) above for measuring the electric currents were repeated.

Comparison between the corrected electric current value obtained in Test (A) and that obtained in Test (B) showed that the corrected electric current value of Test (B) was only 73% of that of Test (A).

In spite of the fact that the enzyme electrode used in Test (B) above contained larger amounts of the enzymes in terms of the activities thereof, the sensitivity of the enzyme electrode was lowered when the total amount of proteins in the portion of the reaction layer which portion is superposed on the working electrode exceeded an optimum amount.

REFERENCE EXAMPLE 3

The effect of the total amount of proteins on the sensitivity of the enzyme electrode was examined with respect to a portion of the reaction layer which is superposed on the working electrode.

Test (C):

An enzyme electrode was prepared in substantially the same manner as in Test (A) of Reference Example 2, except that an aqueous solution containing 15.5 mg/ml (670 U/ml) of DI (which is the same as used in Reference Example 1), 7.4 mg/ml (1,700 U/ml) of 12α-HSD (which is the same as used in Reference Example 1), 7.4 mg/ml (170 U/ml) of NADS (which is the same as used in Reference Example 1) and 9.35 mg/ml of BSA was applied to the CMC layer to thereby form a reaction layer. The total amount of protein was 1.49 mg per cm$^2$ of the reaction layer (and the amounts of the enzymes in terms of the activities thereof were the same as in Test (B) above).

Using the prepared enzyme electrode, the same operations as conducted in Test (A) of Reference Example 2 for measuring the electric currents were repeated.

Tests (D) to (F):

Enzyme electrodes were prepared in substantially the same manner as in Test (C) above, except that the concentration of BSA in the aqueous solution was varied so as to form the reaction layers having different total protein contents. The BSA concentrations of the aqueous solutions used in tests (D) to (F) were 18.8 mg/ml, 25.0 mg/ml and 50.0 mg/ml, respectively. Accordingly, the total amounts of proteins were, respectively, 1.84 mg, 2.07 mg and 3.01 mg per cm$^2$ of the reaction layer (and the amounts of the enzymes in terms of activities thereof were the same as in Test (B) above).

Using each of the prepared enzyme electrodes, the same operations as conducted in Test (C) above for measuring the electric currents were repeated.

The comparison between the corrected electric current value obtained in Test (A) of Reference Example 2 and each of the corrected electric current values obtained in Tests (C) to (F) above showed that the corrected electric current values for test Tests (C) to (F) were, respectively, 57%, 38%, 22% and 5% of that of Test (A).

From this fact, it became apparent that, when the total amount of proteins in the portion of the reaction layer which portion is superposed on the working electrode exceeds a specific range, the higher the total protein content of the reaction layer, the lower the sensitivity of the enzyme electrode.

REFERENCE EXAMPLE 4

The effect of the amounts of the enzymes in terms of the activities thereof on the sensitivity of the enzyme electrode was examined with respect to a portion of the reaction layer which is superposed on the working electrode.

Tests (G) to (J):

Enzyme electrodes were prepared in substantially the same manner as in Test (A) of Reference Example 2, except that the aqueous solution used for preparing the reaction layer was diluted before applying to the CMC layer. Specifically, the aqueous solution as used in Test (A) was diluted 2-, 4-, 16- and 80-folds before using in Tests (G) to (J), respectively (thus, the amounts of enzymes in terms of the activities thereof were ½, ¼, ⅟₁₆ and ⅟₈₀ of the reaction layer formed in Test (A) of Reference Example 2).

Using each of the prepared enzyme electrodes, the same operations as conducted in Test (A) above for measuring the electric currents were repeated.

Comparison between the corrected electric current values obtained in Test (A) of Reference Example 2 and each of the corrected electric current values obtained in Tests (G) to (J) above showed that the corrected electric current values for Tests (G) to (J) were, respectively, 63%, 47%, 33% and 4% of that of Test (A).

From this fact, it became apparent that, with respect to the portion of the reaction layer which portion is superposed on the working electrode, the lower the amounts of enzymes in terms of the activities thereof, the lower the sensitivity of the enzyme electrode.

INDUSTRIAL APPLICABILITY

The enzyme electrode of the present invention is advantageous for miniaturizing an apparatus for determining the concentration of ATP. Further, by the use of the enzyme electrode of the present invention, it has become possible to perform a determination of the ATP concentration of a sample easily and rapidly, with high sensitivity, without the need of a cumbersome pretreatment.

The invention claimed is:

1. An enzyme electrode comprising:
   (a) an electrode system comprising an insulating substrate having formed thereon a working electrode, a counter electrode and optionally a reference electrode; and
   (b) a reaction layer formed on said electrode system, wherein said reaction layer comprises diaphorase (DI), 12α-hydroxysteroid dehydrogenase (12α-HSD) and nicotinamide adenine dinucleotide synthetase (NADS), at least a portion of said reaction layer being superposed on said working electrode, wherein the DI, 12α-HSD and NADS contained in said portion of the reaction layer are immobilized on the surface of said working electrode, so that a compound generated in said reaction layer can reach the surface of said working electrode, and wherein, with respect to said portion of the reaction layer which is superposed on said working electrode;
   the total amount of proteins is 2.5 mg or less per $cm^2$ of said portion of said reaction layer;
   the amount of DI in terms of the activity thereof is 0.25 U or more per $cm^2$ of said portion of said reaction layer;
   the amount of 12α-HSD in terms of the activity thereof is 0.63 U or more per $cm^2$ of said portion of said reaction layer; and
   the amount of NADS in terms of the activity thereof is 0.063 U or more per $cm^2$ of said portion of said reaction layer.

2. The enzyme electrode according to claim 1, which further comprises a hydrophilic polymer layer, said hydrophilic polymer layer being interposed between said working electrode and said reaction layer and being in contact with both of said working electrode and said reaction layer.

3. The enzyme electrode according to claim 1 or 2, wherein, with respect to said portion of the reaction layer which is superposed on said working electrode:
   the total amount of proteins is 1.5 mg or less per $cm^2$ of said portion of said reaction layer;
   the amount of DI in terms of the activity thereof is 1.0 U or more per $cm^2$ of said portion of said reaction layer;
   the amount of 12α-HSD in terms of the activity thereof is 2.5 U or more per $cm^2$ of said portion of said reaction layer; and
   the amount of NADS in terms of the activity thereof is 0.25 U or more per $cm^2$ of said portion of said reaction layer.

4. The enzyme electrode according to claim 1 or 2, wherein, with respect to said portion of the reaction layer which is superposed on said working electrode:
   the total amount of proteins is 1.1 mg or less per $cm^2$ of said portion of said reaction layer;
   the amount of DI in terms of the activity thereof is 2.5 U or more per $cm^2$ of said portion of said reaction layer;
   the amount of 12α-HSD in terms of the activity thereof is 6.25 U or more per $cm^2$ of said portion of said reaction layer; and
   the amount of NADS in terms of the activity thereof is 0.625 U or more per $cm^2$ of said portion of said reaction layer.

5. A method for determining the concentration of adenosine triphosphate (ATP) in a sample, which comprises:
   mixing a sample with an aqueous solution containing nicotinic acid adenine dinucleotide, a bile salt, an electron carrier and at least one member selected from the group consisting of ammonia and ammonium ion, to thereby obtain a sample solution;
   contacting said sample solution with said working electrode, counter electrode and optionally reference electrode of the enzyme electrode of claim 1 or 2, to thereby form an electric circuit through said sample solution;
   measuring the electric current at said working electrode while applying a voltage to said enzyme electrode between the working electrode thereof and the counter electrode thereof or between the working electrode thereof and the reference electrode thereof to thereby perform an oxidation reaction of said electron carrier on the surface of said working electrode, wherein when said enzyme electrode does not contain a reference electrode, said voltage is applied between said working electrode and said counter electrode and wherein when said enzyme electrode contains a reference electrode, said voltage is applied between said working electrode and said reference electrode; and calculating the amount of ATP, based on the measured value of said electric current at said working electrode.

6. A system for determining the concentration of adenosine triphosphate (ATP) in a sample, wherein said concentration of ATP is determined using nicotinic acid adenine dinucleotide, a bile salt, an electron carrier and at least one member selected from the group consisting of ammonia and ammonium ion, said system comprising:

the enzyme electrode of claim 1 or 2;

means for applying a voltage to said enzyme electrode between the working electrode thereof and the counter electrode thereof or between the working electrode thereof and the reference electrode thereof, said voltage being sufficient to perform an oxidation reaction of said electron carrier on the surface of said working electrode; and means for measuring the electric current at said working electrode.

7. The system according to claim 6, which further comprises means for calculating the amount of ATP, based on the measured value of said electric current at said working electrode.

* * * * *